United States Patent
Lejano et al.

(10) Patent No.: US 8,595,097 B2
(45) Date of Patent: Nov. 26, 2013

(54) AUTOMATIC AD GROUP CREATION IN A NETWORKED ADVERTISING ENVIRONMENT

(75) Inventors: Lisandro Miguel Lejano, Foster City, CA (US); Erik Ruben Racho, Arcadia, CA (US); Claude Jones, San Marcos, CA (US)

(73) Assignee: Yahoo! Inc., Sunnyvale, CA (US)

( * ) Notice: Subject to any disclaimer, the term of this patent is extended or adjusted under 35 U.S.C. 154(b) by 934 days.

(21) Appl. No.: 12/130,442

(22) Filed: May 30, 2008

(65) Prior Publication Data

US 2009/0300031 A1    Dec. 3, 2009

(51) Int. Cl.
*G06Q 40/00* (2012.01)

(52) U.S. Cl.
USPC .............................. 705/35; 705/40

(58) Field of Classification Search
USPC .............................. 705/14, 35, 40
See application file for complete search history.

(56) References Cited

U.S. PATENT DOCUMENTS

| | | | |
|---|---|---|---|
| 6,026,368 A | 2/2000 | Brown et al. | |
| 6,167,382 A | 12/2000 | Sparks | |
| 6,230,173 B1 | 5/2001 | Ferrel et al. | |
| 6,253,188 B1 | 6/2001 | Witek et al. | |
| 6,269,361 B1 | 7/2001 | Davis et al. | |
| 6,401,075 B1 | 6/2002 | Mason et al. | |
| 7,231,358 B2 | 6/2007 | Singh et al. | |
| 7,958,040 B2 | 6/2011 | Jain et al. | |
| 2001/0013004 A1 | 8/2001 | Haris et al. | |
| 2002/0073034 A1 | 6/2002 | Wagner et al. | |
| 2004/0103024 A1 | 5/2004 | Patel et al. | |
| 2005/0010477 A1 | 1/2005 | Sullivan et al. | |

(Continued)

FOREIGN PATENT DOCUMENTS

| | | |
|---|---|---|
| JP | 2002354444 A2 | 12/2002 |
| KR | 2002000922 | 1/2002 |

(Continued)

OTHER PUBLICATIONS

Newsbytes News Network; "AdOptimizer—Ad Management Software for Websites"; Oct. 4, 1996; Supplier Number: 23663696.*

(Continued)

*Primary Examiner* — Edward Chang
(74) *Attorney, Agent, or Firm* — Brinks Gilson & Lione

(57) ABSTRACT

A method for organizing an advertising campaign in an Internet environment is provided. The method may include displaying, on a display device, a list of web sites that have attributes that match received selection criteria. The method may also include selecting at least one web site in the list and specifying purchasing information for purchasing advertising space on the at least one web site, associating the at least one web site and the specified purchasing information with an ad group. The web sites in the ad group may have attributes that match the received selection criteria. The ad group may be stored in a memory. The selection criteria may have come by way of an order from an advertiser and may include advertising space position information, demographic information, behavioral information, geographic information, technology information, and web site content information.

25 Claims, 14 Drawing Sheets

(56) References Cited

U.S. PATENT DOCUMENTS

| | | | |
|---|---|---|---|
| 2005/0027594 A1* | 2/2005 | Yasnovsky et al. | 705/14 |
| 2005/0197918 A1 | 9/2005 | Wittmer et al. | |
| 2006/0242013 A1 | 10/2006 | Agarwal et al. | |
| 2007/0198341 A1* | 8/2007 | Park | 705/14 |
| 2007/0214048 A1 | 9/2007 | Chan et al. | |
| 2007/0276732 A1 | 11/2007 | Lee et al. | |
| 2008/0126515 A1* | 5/2008 | Chambers et al. | 709/218 |
| 2008/0294524 A1 | 11/2008 | Badros et al. | |
| 2009/0132346 A1 | 5/2009 | Duggal et al. | |

FOREIGN PATENT DOCUMENTS

| | | |
|---|---|---|
| KR | 10-2002-0067940 | 8/2002 |
| KR | 2005053057 | 6/2005 |
| KR | 10-2006-0052853 | 5/2006 |
| WO | WO 98/34189 A1 | 8/1998 |
| WO | WO 99/62013 A1 | 12/1999 |
| WO | WO 2005/010702 | 2/2005 |

OTHER PUBLICATIONS

Business Wire; "Internet Wine Marketing Roundtables Scheduled for Marketing Winery Web Sites"; Sep. 27, 2000; Supplier Number: 65510656.*

Kohda, Youji et al., "Ubiquitous advertising on the WWW: Merging advertisement on the browser," *Computer Networks and ISDN Systems 28*, 1996, pp. 1493-1499.

Written Opinion of the International Searching Authority for PCT/US2009/042581, Date of Mailing Oct. 26, 2009.

First Office Action from corresponding Chinese Patent Application No. 200980118849.6, 10pp., Oct. 29, 2012.

KIPO Notice of Preliminary Rejection and English Translation from corresponding Korean patent application No. 10-2010-7026672, 9pp., Jul. 26, 2012.

First Office Action from corresponding Chinese Patent Application No. 200980118849.6, 4pp., Feb. 2, 2012.

Extended European Search Report for European Application No. 09758900.6 mailed Oct. 28, 2011.

* cited by examiner

Search Results 500 — 540 Filter

| Add Placements 515 | Sites | 520 Category | 525 Bookable Impressions | 530 Floor CPM | 535 Target CPM | 545 List CPM |
|---|---|---|---|---|---|---|
| Add $ | Columbus Dispatch | Sports | 20,000 | $5.25 | $6.25 | 7.25 |
| ▼ $ | Media General | Sports | 20,000 | $5.25 | $6.25 | 7.25 |
| Add $ | Bello Press Enterprise | Sports | 20,000 | $5.25 | $6.25 | 7.25 |
| Add $ | Palm Beach News | Sports | 20,000 | $5.25 | $6.25 | 7.25 |
| Add $ | Calkins | Sports | 20,000 | | | |
| Add $ | Online Prints | Sports | | | | |

1-6 of 6   First | < Prev | Next > | Last

Ad Group Workspace 510 — 595 More actions

Name: Sports Males 550
Targeting: Males 17-25; who visit Sport sites in live in California. 555

| Sites 560 | Category | Position | Ad Dimension 565 | Flight Dates 570 | CPM 575 | Impressions 580 | Cost 585 |
|---|---|---|---|---|---|---|---|
| ☐ Media Gen... | Sports | North | 160 x 600 (Wide Skysc... | 12/01/2007- 01/31/2008 | $6.25 | 20,000 | $2000 |
| ☐ Bello Pre... | Sports | North | 160 x 600 (Wide Skysc... | 12/01/2007- 01/31/2008 | $6.25 | 20,000 | $1000 |
| ☐ Calkins | Sports | North | 160 x 600 (Wide Skysc... | 12/01/2007- 01/31/2008 | $6.25 | 20,000 | $500 |
| ☐ Online Prints | Sports | North | 160 x 600 (Wide Skysc... | 12/01/2007- 01/31/2008 | $6.25 | 20,000 | $500 |

1-1 of 1   First | < Prev | Next > | Last

Total Consumed: $5000   590

Return to Order

Fig. 5

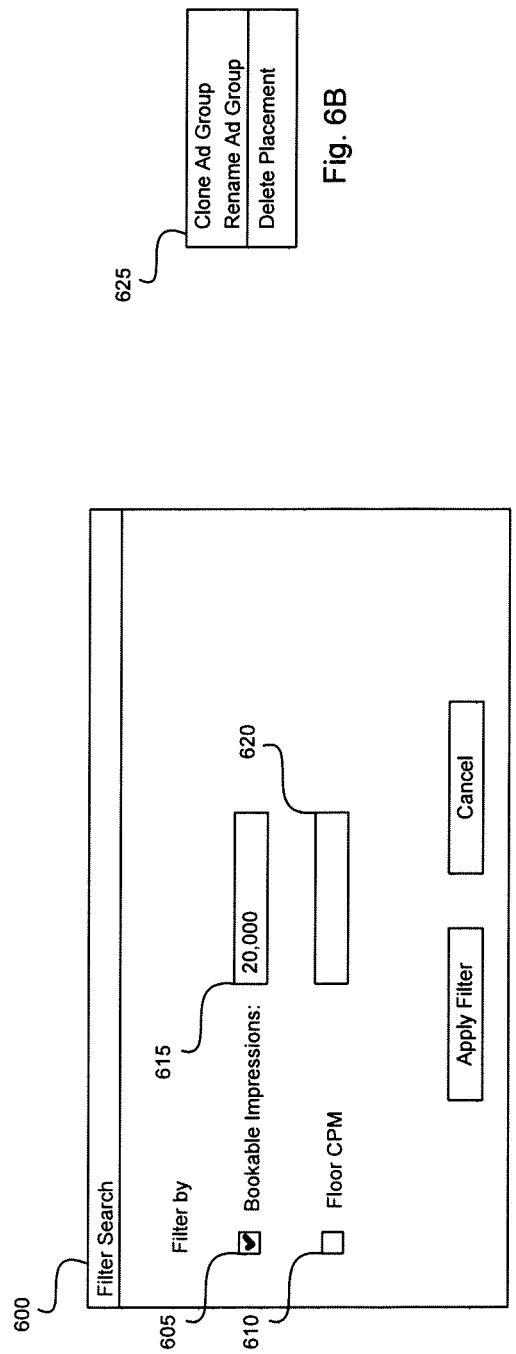

Fig. 9

Search Results

| Add Placements | Network | Category | Bookable Impressions | Floor CPM | Target CPM | List CPM |
|---|---|---|---|---|---|---|
| ☑ $ | Yahoo network 1 | Sports | 20,000 | $5.25 | $6.25 | 7.25 |
| Add $ | XYZ network | Sports | 20,000 | $5.25 | $6.25 | 7.25 |
| Add $ | ABC network | Sports | 20,000 | $5.25 | $6.25 | 7.25 |

1-6 of 6    First | <Prev | Next > | Last

Filter

Ad Group Workspace

Name: Sports Males
Targeting: Males 17-25; who visit Sport sites in live in California.

| | Network | Category | Position | Ad Dimension | Flight Dates | CPM | Impressions | Cost |
|---|---|---|---|---|---|---|---|---|
| ☐ | Yahoo network 1 | Sports | North | 160 x 600 (Wide Skysc... | 12/01/2007- 01/31/2008 | $20.00 | 10,000 | $200,000 |
| | | | | | | Total Consumed: | | $200,000 |

1-1 of 1    First | <Prev | Next > | Last

Return to Order          More actions

Fig. 10

AUTOMATIC AD GROUP CREATION IN A NETWORKED ADVERTISING ENVIRONMENT

RELATED APPLICATIONS

The present application relates to applications entitled: "SUPPLY CURVE PRICING IN A NETWORKED ADVERTISING ENVIRONMENT," (U.S. Patent Publication No. 2009/0299798 A1) filed on May 30, 2008; "PLACEMENT PRICING IN A NETWORKED ADVERTISING ENVIRONMENT," (U.S. Patent Publication No. 2009/0299799 A1) filed on May 30, 2008; "SYSTEM FOR DISPLAYING INVENTORY SEARCH PARAMETERS FOR AN ADVERTISER," (U.S. Patent Publication No. 2009/0307085 A1) filed on May 30, 2008; and "SYSTEM FOR DISPLAYING A POSITION VIEWER FOR PREVIEWING THE DISPLAY OF AN ADVERTISEMENT," (U.S. Patent Publication No. 2009-0300490 A1) filed on May 30, 2008.

BACKGROUND

The Internet has emerged as a powerful advertising tool. It is common place to see advertisements on many web sites. For example, advertisements may be displayed on search web sites and may be targeted to individuals based upon search terms provided by the individuals. Other web sites, such as news and sports web sites, may provide space for advertisements. The owners of these web sites may sell advertising space to advertisers to offset the costs associated with operating the web sites as well as to turn a profit.

As the internet has grown, the number of web sites available for hosting advertisements has increased. The diversity between web sites has also increased. That is, the number of web sites focusing on selective groups of individuals has increased. For example, some web sites cater to gaming enthusiasts. Some may cater to women in a certain age group. As a result of the increase, it has become increasingly difficult for advertisers to optimize their advertising budgets. For example, some web sites may be better suited to a particular advertiser's products than others. Advertisers unfamiliar with the vast number of web sites available for hosting advertisements may choose to host their respective advertisements on a less than optimal host web site. This may result in a lower rate of return for the advertiser. The advertiser may have received a greater rate of return had the advertiser chosen a more suitable host web site.

BRIEF DESCRIPTION OF THE DRAWINGS

FIG. 5 is an exemplary search result user interface for displaying a list of publisher web sites that may be suitable for displaying advertiser advertisements;

FIG. 6A is a filter box user interface that may be utilized to refine the list of publisher web sites shown in the search result user interface;

FIG. 6B is a pop up menu for editing an ad group;

FIG. 9 is a second embodiment of an exemplary search result user interface for displaying a list of networks that may be suitable for displaying advertiser advertisements;

FIG. 10 is a price placement user interface that may be utilized for purchasing advertisement placements in a network;

DETAILED DESCRIPTION OF THE DRAWINGS AND THE PRESENTLY PREFERRED EMBODIMENTS

Figure 1:
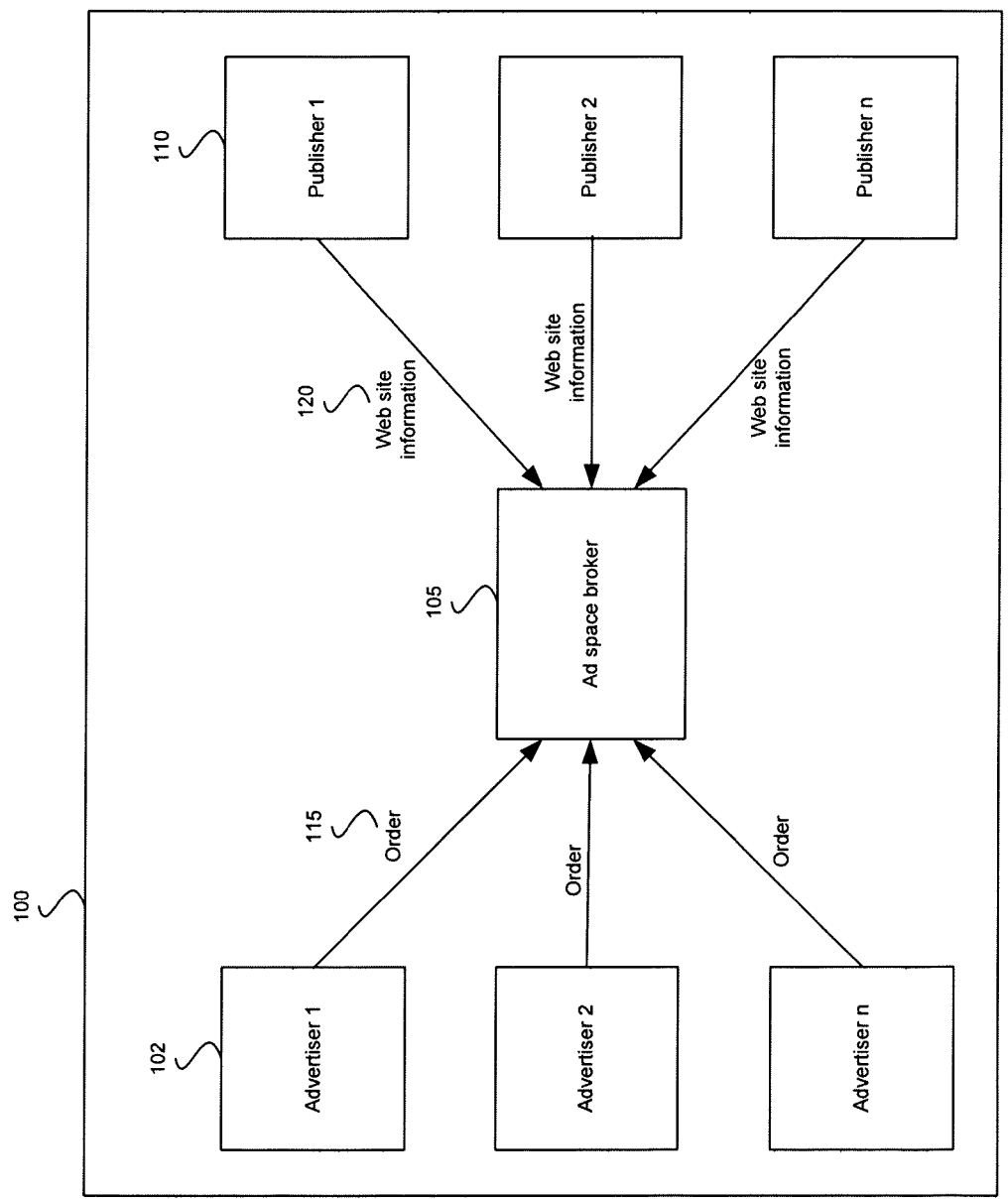
FIG. 1 is a diagram illustrating the relationship between an ad space broker, advertisers, and publishers.

FIG. 1 is a diagram 100 illustrating the relationship between an ad space broker 105, advertisers 102, and publishers 110. The ad space broker 105 may receive advertiser orders 115 from advertisers 102 seeking to have their respective advertisements displayed on publisher 110 web sites. The advertiser orders 115 may include audience targeting information. For example, demographic, behavioral, and geographic information may be specified in the order. The demographic information may be utilized to target certain age groups and genders. The behavioral information may be utilized to target individuals with certain buying preferences. The geographic information may be utilized to target individuals in a particular geographic location. The advertisers 102 may also provide information that may be utilized to target individuals that utilize a particular technology. For example, the advertisers 102 may wish to target individuals who utilize a particular Internet browser, computer, and/or operating system. The advertisers 102 may also specify information for positioning an advertisement. For example, the advertiser 102 may want advertisements displayed on the top of a web page that operates on a publisher's 110 web site. The advertiser 100 may also include budget information. The budget information may correspond to a maximum amount of money that an advertiser 100 may be willing to spend on an advertising campaign. The orders 115 from the advertisers 102 may include other information as well and may be presented in any suitable format, such as a hypertext markup language (HTML) page conveyed from an advertiser 102 to the ad space broker 105.

The ad space broker 105 may receive web site information 120 from publishers 110 that operate web sites with web pages that display advertisements. The web site information 120 may include advertisement position information that may correspond to a position on a web page for displaying advertisements. For example, the position information may indicate that advertisements may be displayed on the top or sides of the web page. The web site information 120 may also include information related to a respective target audience for the web site. For example, the publishers 110 may provide demographic, behavioral, and geographic information related to their respective audiences. The publishers 110 may also specify the technology utilized by their audience in accessing the publisher's 110 web sites. For example, a particular publisher's 110 web site may only be suited for a particular Internet browser or products sold via the publishers 110 web site may only be for a specific type of hardware. The publishers 110 may also provide rate card information related to the web site. The rate card information may correspond to a range of prices for displaying advertisements on the publisher's web sites. For example, the rate card information may include a floor, target and list CPM (cost per thousand impressions). An impression corresponds to displaying an advertisement on a publisher web page, clicking on an advertisement, or purchasing goods or services after clicking on an advertisement. The floor CPM may correspond to the minimum price the publisher 110 may be willing to accept. The list CPM may correspond to the same price that the publisher 110 may charge when the publisher sells advertising space directly to advertisers. The target CPM may correspond to a target selling price that an ad space broker 105 may try to achieve for the impressions.

In operation, the ad space broker 105 may receive advertiser orders 115 for placing advertisements from advertisers 100. The advertiser orders 115 may include demographic, behavioral, geographic and technology information for an audience the advertiser 100 may be targeting as described above. The advertiser orders 115 may also include budget information related to the maximum amount the advertisers 100 may be willing to spend on advertising. The ad space broker 105 may also receive web site information 120 from publishers 110. The web site information 120 may include advertisement position, demographic, behavioral, geographic, and technology information as described above. The web site information 120 may also include a desired price that the publisher 110 wishes to obtain for the placement of advertisements.

The ad space broker 105 may then match advertiser orders 115 to publisher 110 web sites based on information provided in the advertiser orders 100 and the web site information 120. After matching advertiser orders 115 with publisher 110 web sites, a link to an ad server may be provided to the publishers 110. The link may enable communicating advertiser 100 advertisements from the ad server to web pages generated by the publishers 110. The link may be embedded within the browser code utilized to render the web pages and may enable the Internet browser to retrieve the advertisement from the ad server.

Figure 2:
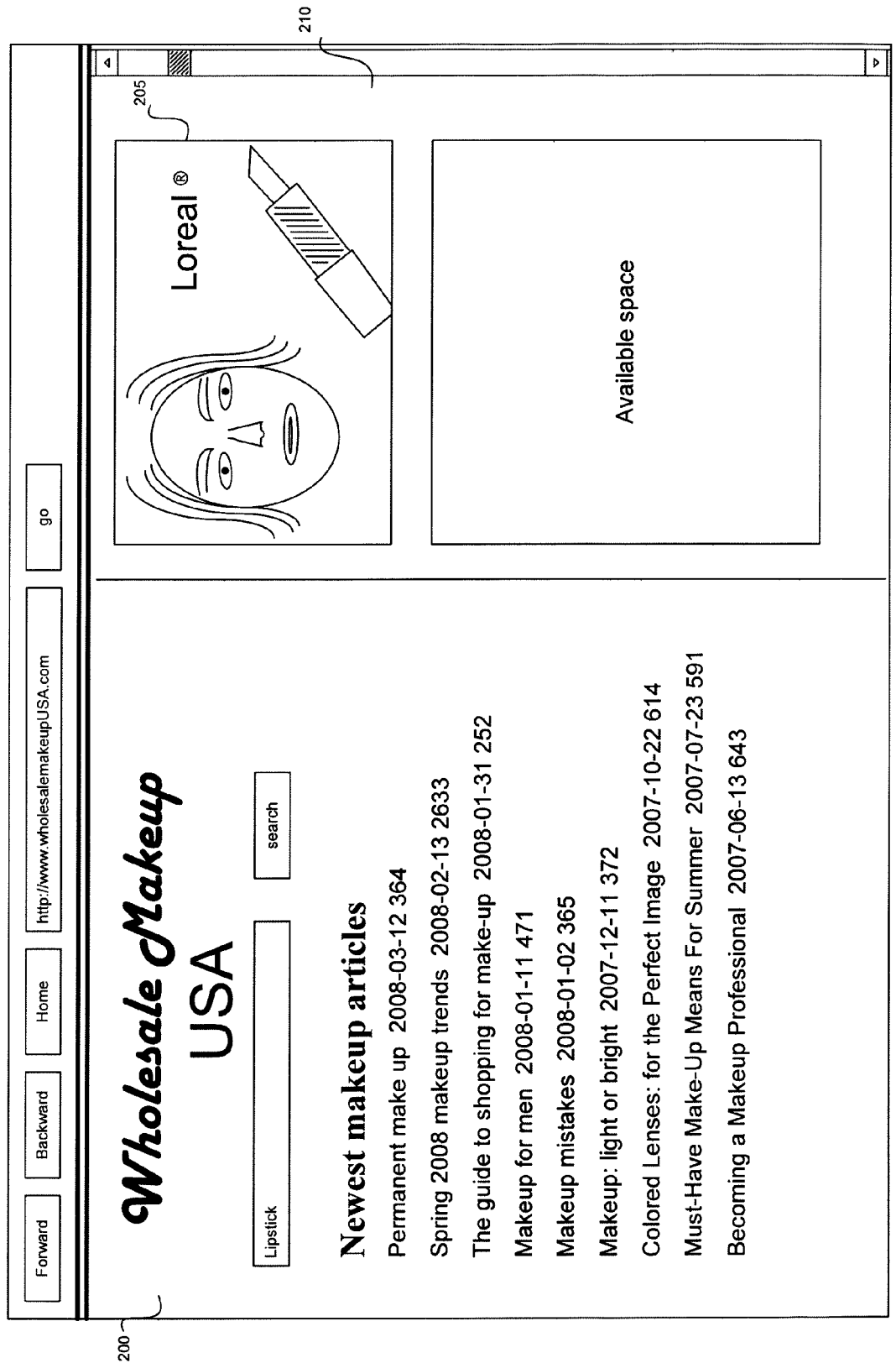
FIG. 2 is an exemplary publisher web page.

FIG. 2 is an exemplary publisher web page 200. The web page 200 may include an advertisement region 210 with an advertisement 205. The publisher of the web page 200 may have provided demographic and/or behavioral information that indicated that women interested in makeup frequent the web page 200. The publisher may have provided position information corresponding to the advertisement region 210 of the web page 200. For example, in this case the publisher may have specified that advertisements may be displayed on the right side of the web page 200. A link to an ad server for communicating advertisements may have been provided to the publisher. In this case, the ad server may have communicated a makeup advertisement. The advertiser associated with the advertisement 205 may have previously provided, as part of an advertiser order 115, audience targeting information that specified the target audience as woman who purchase makeup. By displaying the advertisements the publisher of the web site hosting the web page 200 may subsidize the costs associated with operating the web site and may also turn a profit.

Figure 3:
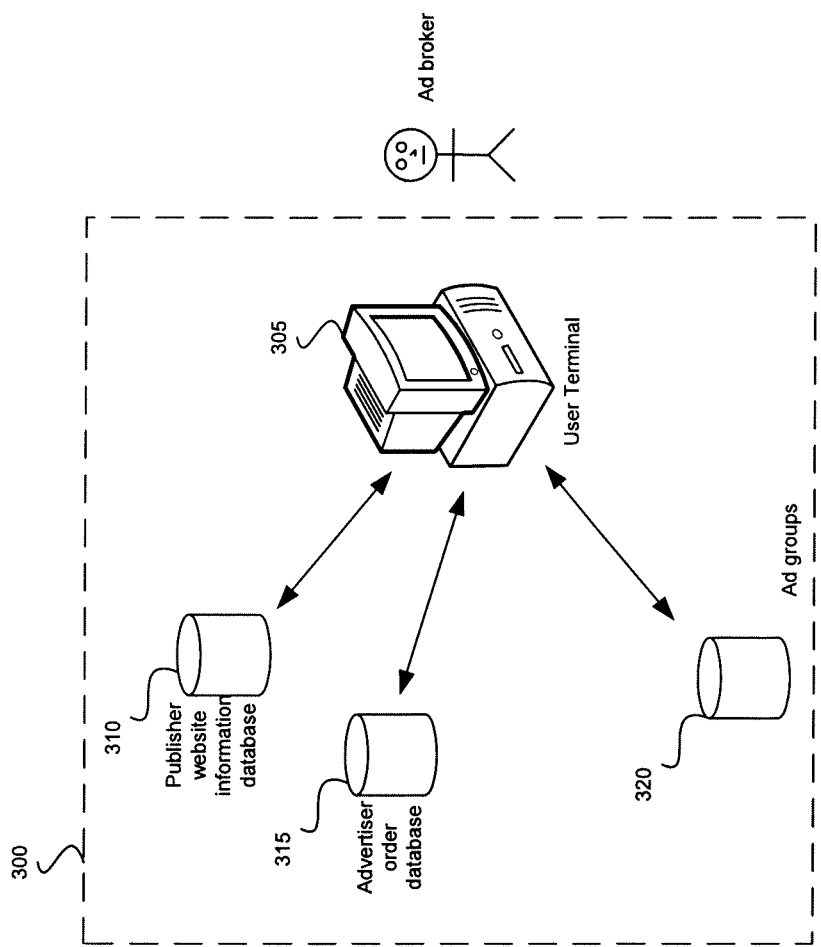
FIG. 3 is a system that may be utilized by an ad broker to enable matching advertiser advertisements to publisher web sites.

FIG. 3 is a system 300 that may be utilized by an ad broker to enable matching advertiser advertisements to publisher web sites. The system 300 includes a computer 305 in communication with a publisher web site information database 310, an advertiser order database 315, and an ad group database 320. The computer 305 may comprise suitable logic, code, and/or circuitry that may enable operating a computer program for performing the operations described above. For example, the computer 305 may be configured to communicate order information from advertisers and web site information from publishers. The system 300 may be adapted to store the information communicated into a database. For example, information related to publisher web sites may be stored in the publisher information database 310 and advertiser orders may be stored in the advertiser order database 315.

The computer 305 may also be configured to execute an application for matching orders communicated from the advertisers to publisher web sites. For example, the application may enable the entry of advertiser orders and publisher web site information. The application may store information in the advertiser order and publisher web site information databases 315 and 310 respectively. The application may then enable searching through the publisher web site information database 310 for publisher web sites that may be suitable for displaying an advertiser advertisement. For example, via the application, the ad broker may specify a desired position for an advertisement. The ad broker may also specify demographic, behavioral, geographic, and technology information corresponding to the target audience for the advertisement.

The computer 305 may also be configured to execute an application that enables booking advertisement placements on the publisher websites and adding the publisher web sites to the ad group database 320. For example, the application may enable specifying the number of impressions, cost per impression, and total cost associated with booking the advertisement placements. After specifying the information, the publisher web site may be added to an ad group of publisher web sites and saved to the ad groups database 320. The publisher web sites in the ad group may be related in that the publisher web sites may share various attributes. For example, the publisher web sites may all target a particular demographic group. Grouping and saving the publisher web sites in an ad group may enable quickly purchasing placement for similar ads. For example, an ad group may have been created for targeting a particular advertisement to males between the ages of 20 and 30. Later, an advertiser may wish to place new advertisements to the same group. In this case, the ad broker may link the new advertisement to the ad group without having to repeat a search for publisher web sites that match the desired target audience.

Figure 4:
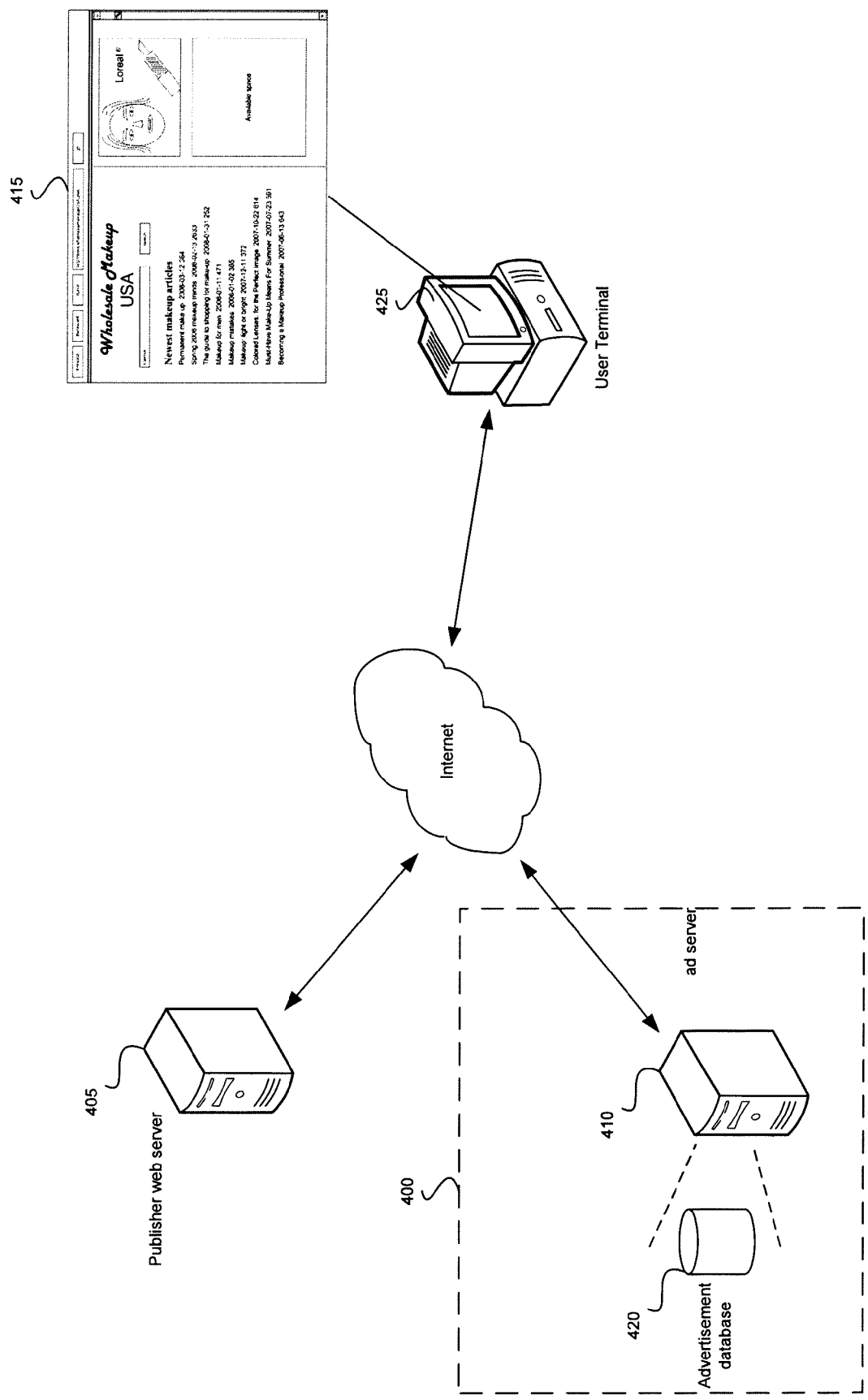
FIG. 4 is a system for communicating advertisements to web pages generated by publisher web sites.

FIG. 4 is a system 400 for communicating advertisements to web pages generated by publisher web sites. The system 400 includes an ad server 410 and an advertisement database 420. The system 400 communicates with a publisher web sever 405 as is also shown in FIG. 4. The publisher web server 405 may include suitable logic, code, and/or circuitry that may enable communicating web pages to an Internet browser 415 operating on a user terminal 425. For example, the publisher web server 405 may correspond to a computer with an operating system, such as Windows® or Linux. An application, such as Apache®, may operate on the publisher web site and may enable communicating web page information to Internet browsers. The web page information may include web page content information, such as graphics, audio, and text. The web page information may also include execution instructions that may enable retrieving advertisements from the ad server 410.

The ad server 410 may include suitable logic, code, and/or circuitry that may enable selecting and communicating advertisements to an Internet browser 415. For example, the ad server 410 may correspond to a computer with an operating system, such as Windows® or Linux that may be suitable for hosting an advertisement server application. The advertisement server application may enable communicating advertisements to Internet browsers. The ad server 410 may include or be in communication with an advertisement database 420. The advertisement database 420 may include advertisement content data, such as graphics, text, and/or audio that may be communicated to the Internet browser 415. The advertisement content data may also include publisher web site targeting data that may be utilized to associate the advertisement with publisher web sites. The publisher web sites may have been previously associated with the advertisement via the system 300 (FIG. 3) described above.

In operation, a request to display a web page may be communicated from the Internet browser 415 to the publisher web server 405. In response, the publisher web server 405 may communicate a web page to the Internet browser 415. The web page communicated may include execution instructions for retrieving an advertisement. The execution instructions may enable communicating an advertisement from the ad server 410 to the Internet browser 415. In doing so, the Internet browser 415 may communicate publisher web site identifying data to the ad server 410. This may allow the ad server 410 to determine the identity of the publisher web site corresponding to the web page being displayed on the Internet browser 415. Upon receiving the publisher web site identifying data, the ad server 410 may search through the advertisement database 420 for an advertisement that may be associated with the publisher web site. After locating such an advertisement, the ad server 410 may communicate the advertisement content data to the Internet browser 415.

FIG. 5 is an exemplary search result user interface 500 for displaying a list of publisher web sites that may be suitable for displaying advertiser advertisements. The search result user interface 500 may be generated by the application operating on the computer 305 shown in FIG. 3. The search result user interface 500 may include a search result region 505 and an ad group region 510. The search result region 505 may include a series of columns including a site column 515, a category column 520, a bookable impressions column 525, and floor CPM column 530, target CPM column 535, and list CPM column 545. A filter button 540 may also be shown.

The ad group region 510 may include a series of columns including a site column 550, a category column 555, a position column 560, an ad dimension column 565, a flight dates column 570, a CPM column 575, an impressions column 580, and a cost column 590. The search result user interface may include other types of information or the information may be presented or combined in other ways according to the nature of the information or the requirements of the user.

A list of publisher web sites that match the targeting information provided in an advertiser order may be shown in the search result region 505. For example, the name of the publisher web sites may be shown in the sites column 515. A category for each publisher web site may be shown in the category column 520. For example, the category may be "sports" for a web site related to sports. The number of bookable impressions available for the publisher web sites may be shown in the bookable impressions column 525. The bookable impressions may correspond to the number of impressions a publisher may have available.

Rate card information for each publisher web site may also be shown. The rate card information may correspond to a floor CPM, target CPM, and list CPM associated with the publisher web site. The floor, target, and list CPM for each publisher web site may be shown in the floor CPM column 530, the target CPM column 535 and list CPM column 545. The floor, target and list CPM may correspond to various prices at which impressions may be purchased. Other manners of expressing a purchase price, such as cost per click (CPC) or cost per action (CPA) may be used and illustrated instead or in addition. The floor CPM may correspond to the minimum price a publisher may be willing to accept. The list CPM may correspond to the price at which the publisher may sell advertising space directly to advertisers. The target CPM may correspond to a target selling price that an ad broker may try to achieve for selling the impressions. In other words, to maximize a profit, an ad broker may be motivated to sell impressions for as much as he can. The target CPM may represent the price goal for the ad broker.

A filter button 540 may be provided that may enable narrowing the list of publisher web sites further. Clicking the filter button 540 may bring up the filter box user interface 600 shown in FIG. 6A. Referring to FIG. 6A, the filter box 600 may include a bookable impressions check box 605, a floor CPM check box 610, a bookable impression entry box 615, and a floor CPM entry box 620. Via the bookable impression entry box 615 the ad broker may narrow the list of publisher web sites to those publishers that are capable of providing a certain guaranteed minimum number of impressions. Via the floor CPM entry box 620 the ad broker may narrow the list of publisher web sites to only those publisher web sites that have, for example, a floor CPM less than the value entered. The publisher web site list may be filtered by checking either or both the bookable impressions check box 605 and floor CPM check box 610. Other parameters and values may be specified in the filter box user interface as well. Filtering by bookable impressions and floor CPM is intended to be exemplary only. After the filter value is applied, the publisher list may be limited accordingly. For example, only publisher web sites with the specified number of bookable impressions and/or a floor CPM price below the specified floor CPM may be shown.

Figure 7:
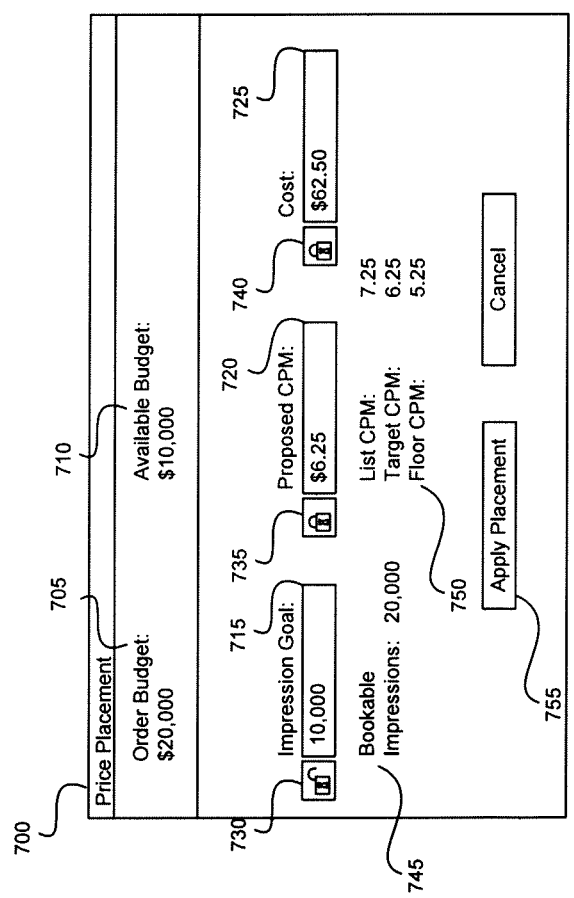
FIG. 7 is a price placement user interface for purchasing advertisement placements.

Returning to FIG. 5, the ad broker may specify an impression goal, a proposed CPM and a total cost to be spent for each publisher website via a user interface, such as the price placement box 700 shown in FIG. 7. Referring to FIG. 7, the price placement box 700 may include an order budget field 705, an available budget field 710, an impression goal entry box 715, a proposed CPM entry box 720, a cost entry box 725, a bookable impressions field 745, a rate card field 750, an impression goal lock 730, a proposed CPM lock 735, and a cost lock 740.

The order budget field 705 may correspond to the total budget specified in an advertiser order and the available budget field 710 may correspond to the amount of the order that has not yet been committed. For example, a budget of $20,000 may be specified in an order and $10,000 may have been previously utilized for purchasing placements on publisher web sites. Displaying the available budget in the price placement box may enable the ad broker to quickly ascertain the amount of budget he may have to work with.

The impression goal entry box 715, proposed CPM entry box 720, and cost entry box 725 may be utilized by the ad broker to specify the number of impressions desired, a proposed CPM for each impressions, and a total cost associated with purchasing the desired impressions at the proposed CPM.

The bookable impressions field 745 may display the total number of impression available for booking impressions on a publisher web site. Displaying the total number of bookable impressions available may enable the ad broker to ascertain the maximum number of impressions he may have to work with.

The rate card field 750 may display the floor, target and list CPM associated with a given publisher web site. Displaying the floor, target and list CPM may enable the ad broker to ascertain a suitable value for the proposed CPM. For example, the floor CPM may correspond to the lowest price per 1000 impressions a publisher may be willing to accept. The list CPM may correspond to the price at which the publisher sells advertising space directly to advertisers.

The number of impressions desired, proposed CPM, and the total cost may be related by the following equation:

$$\text{NumOfImpressions} \times \text{proposed CPM} = \text{total cost}.$$

For example, the total cost for 10,000 impressions at a cost of $6.25 per 1000 impression is $62.50. The impression goal lock 730, proposed CPM lock 735, and cost lock 740 may enable the ad broker to lock the value specified in the impression goal entry box 715, proposed CPM entry box 720, and cost entry box 725 respectively. For example, the ad broker may be more concerned about costs than a specific number of impressions. In this case, the ad broker may lock a value in the cost entry box 725 via the cost lock 740. The ad broker may then specify a desired CPM in the proposed CPM entry box 720 and upon entering a value, the number of impressions may automatically be calculated. In other instances, the ad broker may be more concerned about achieving a certain number of impressions rather than the total cost. In this case, the ad broker may specify and lock the value in the impression goal entry box 715 and unlock the value in the cost entry box 725. As before, the ad broker may then specify a proposed CPM and in this case the total cost may be automatically calculated. In yet another instance, the ad broker may desire a specific number of impression and may also wish to control the total cost. In this case, the ad broker may lock the values specified in the impression goal entry box 715 and cost entry box 725 and unlock the value in the proposed CPM entry box 720. Upon specifying the impression goal and/or the cost, the proposed CPM may be calculated.

Displaying the order budget and available budget along with the number of bookable impressions and the rate card information may allow the ad broker to quickly determine how many impressions to purchase and an optimal price for the impressions. Providing parameter locks may enable the ad broker to lock important parameters and automatically calculate less important parameters. This may further aid the ad broker in determining the number of impressions to purchase and the optimal price for the impressions.

Returning to FIG. 5, the ad broker may add publisher web sites to the ad group region 510. The names of publisher web sites may be displayed in the site column 550. The categories within which the publisher web sites fall may be shown in the category column 555. The location of the advertisement region within publisher web pages may be displayed within the position column 560. For example, the value "North" may be shown when the region for displaying the advertisement is towards the top of the web page. The dimension of an advertisement region within the web page may be shown in the ad dimension column 565. The values shown in the ad dimension column 465 may correspond to the size in pixels of the advertisement region. The dates for displaying the advertisement may be shown in the flight dates column 570. The proposed CPM, impression goal and cost associated with each publisher web site may be shown in the CPM column 575, impression column 480, and cost column 485 respectively. The values in CPM column 575, impression column 580, and cost column 585 may correspond to the values specified via the price placement box 700 (FIG. 7) described above.

The publisher web sites in the ad group region may then be saved under an ad group name. For example a default name, such as "Ad group 1" may be generated. Clicking a more actions button 595 may generate a pop up menu, such as the pop up menu 625 shown in FIG. 6B. The pop up menu 625 may enable changing the name of the ad group to a more descriptive name, such as "Sports Males", as shown in FIG. 5. The pop up menu 625 may also enable cloning or copying an ad group to a new ad group. An example of where cloning may be useful is where some, but not all of the publisher web sites in a base ad group are relevant to a particular advertisement. In this case, the non-relevant publisher web sites may be deleted from the newly cloned ad group. This may enable quickly generating a variety of ad groups that share common attributes with a base ad group. Alternatively, a parent ad group may be created and then cloned. Additional publisher web sites may then be added to the cloned ad groups to create children ad groups. The children ad groups may share target audience information with the parent ad group and may also include target audience information unique to the child ad group.

Figure 8:
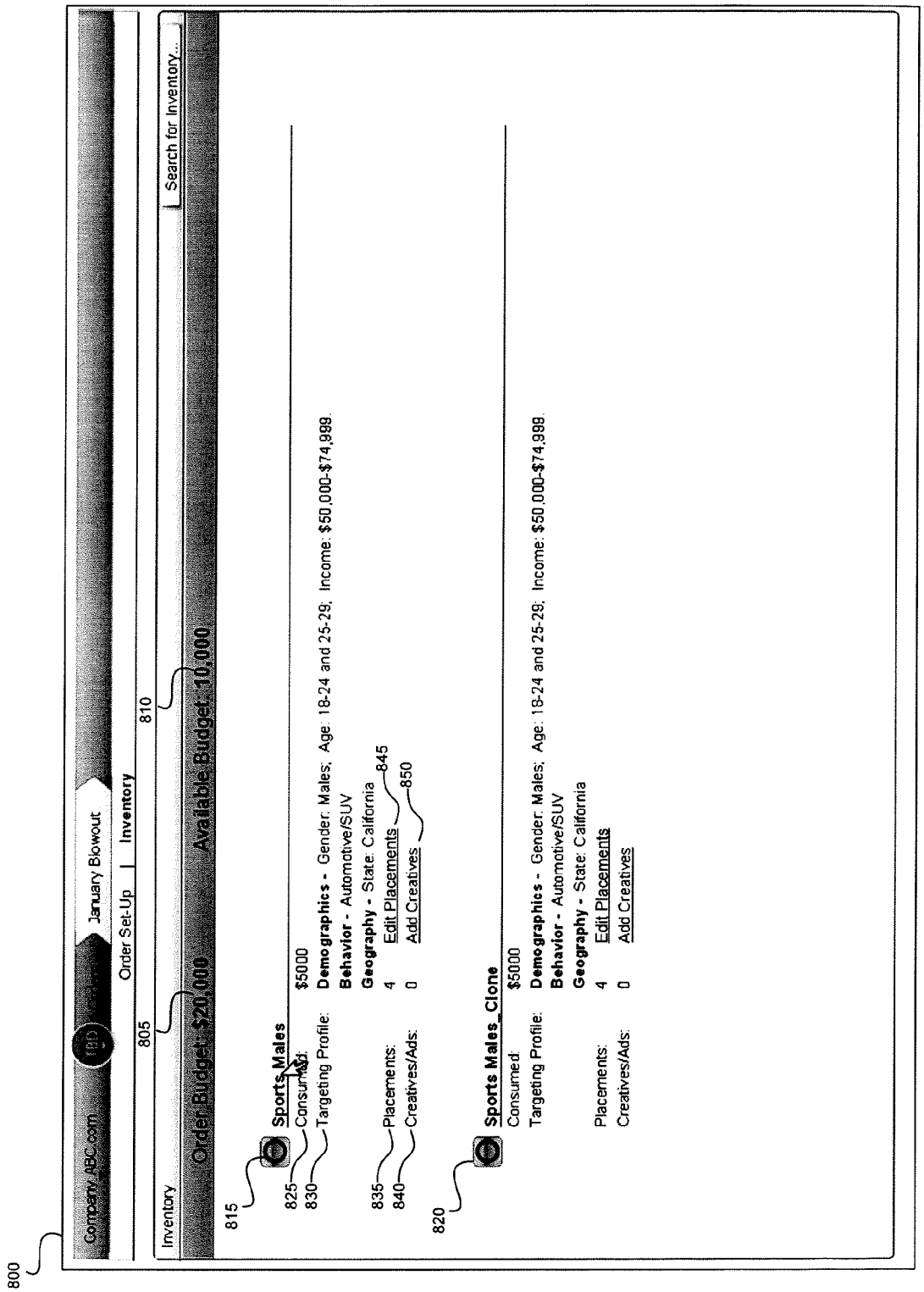
FIG. 8 is an exemplary ad group manager user interface.

FIG. 8 is an exemplary ad group manager user interface 800. The ad group manager user interface 800 may include an order budget field 805, an available budget field 810, and first and second ad group regions 815 and 820. The order budget 805 and available budget 810 may correspond to the total budget for an order and the amount of budget available for making additional placements.

The first and second ad group regions 815 and 820 include an amount consumed field 825, a target profile field 830, a placements field 835, a creatives/ad field 840, an edit placements link 845, and an add creatives link 850. The consumed field 825 may display the total amount of the order budget spent on a particular ad group. The target profiled field 830 may display targeting information associated with the ad group, such as demographic, behavioral, and geographic information. The placements field 835 may display the number of publisher web sites within the ad group and the creatives/ad field may display the number of advertisements associated with the ad group.

The edit placements link 845 may enable editing placements associated with an ad group. For example, the link may direct the ad broker to the search result user interface 500 shown in FIG. 5 and may populate the search result user interface 500 with the publisher web sites in the ad group. From there, the ad broker may add and remove publisher web sites from the ad group. The add creatives link 850 may enable associating advertiser advertisements with the ad group.

The second ad group 820 may correspond to a copied version of the first add group 815. An ad broker may, for example, wish to treat a given ad group as a base ad group and then may create clones of the base ad group and make subtle placement edits to the cloned ad groups. This may enable quickly generating a variety of ad groups that may be focused on a more refined target audience than the original base ad group.

In a second embodiment, advertisers may not be so interested in the identity of the publisher web sites where their respective advertisements may be shown. Rather, the advertisers may be more concerned with obtaining as many impressions as possible for a given price. In this case, impressions may be booked on networks of publisher web sites. FIG. 9 is an exemplary search result user interface 900 for displaying a list of networks that may be suitable for displaying advertiser advertisements. The search result user interface 900 may be generated by the application operating on the computer 305 shown in FIG. 3. The search result user interface 900 may include a search result region 905 and an ad group region 910. The search result region 905 may include a series of columns including a network column 915, a category column 920, a bookable impressions column 925, and floor, target, and list CPM columns 930, 935, and 945. A filter button 940 may also be shown.

The ad group region 910 may include a series of columns including a network column 995, a category column 950, a position column 955, an ad dimension column 960, a flight dates column 965, a CPM column 970, an impressions column 975, and a cost column 980.

A list of networks that include web sites that match the targeting information provided in an advertiser order may be shown in the search result region 905. Each network may correspond to a collection of publisher web sites that may be administered by a network administrator. The name of each network that includes publisher web sites that match the audience targeting information provided in an advertiser order may be shown in the networks column 915. The number of bookable impressions available within the network may be shown in the bookable impressions column 925. The bookable impressions may correspond to the sum of the number of impressions each publisher in the network may be willing to guarantee an advertiser. For example, a publisher may guarantee that an advertisement displayed on the publisher's web site may be displayed 20,000 times during a given time frame.

Figure 10:
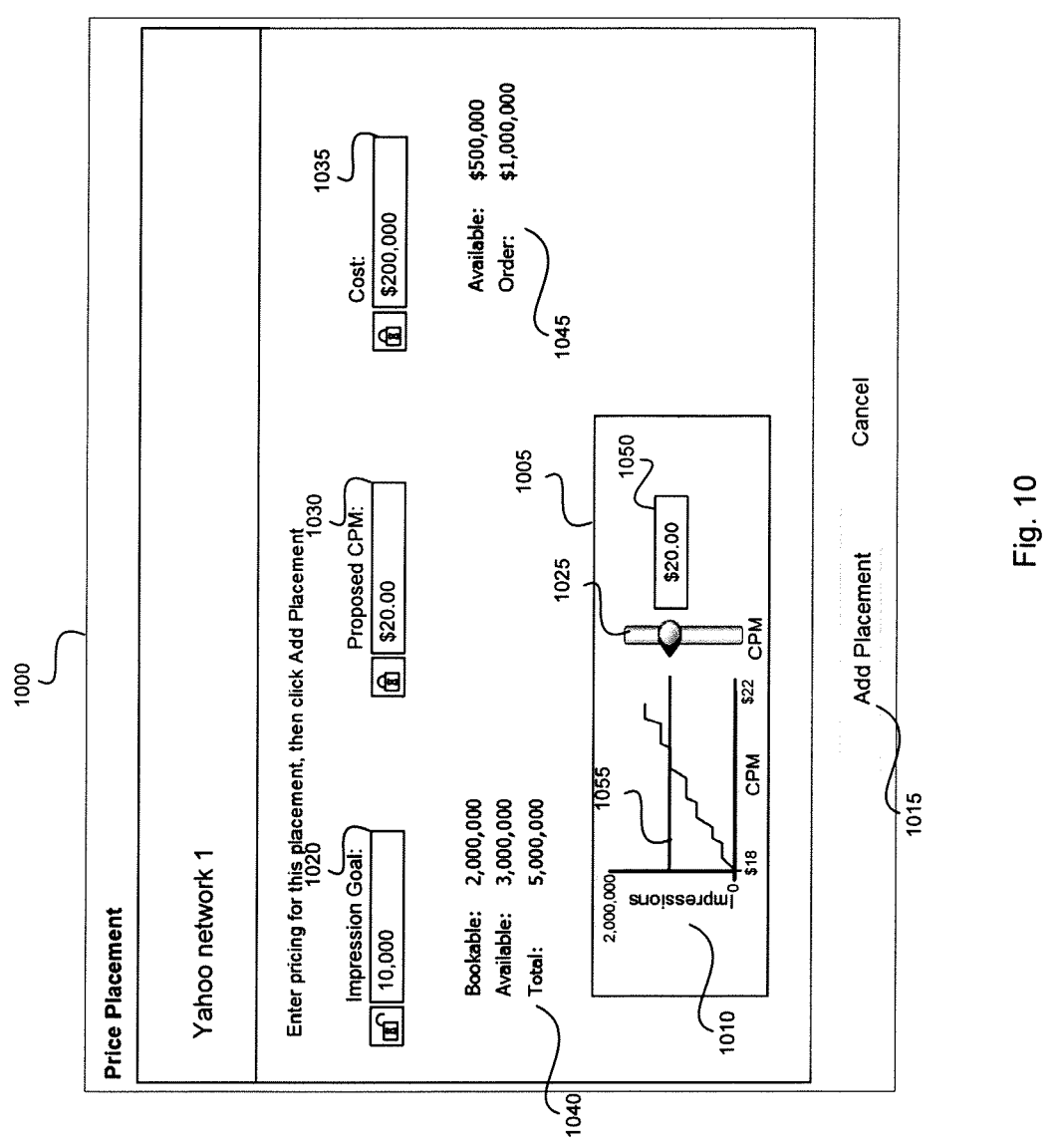

The ad broker may specify an impression goal, a proposed CPM and a total cost to be spent for each network via a user interface, such as the network price placement box 1000 shown in FIG. 10. Referring to FIG. 10, the network price placement box 1000 may include an impression goal entry box 1020, a proposed CPM entry box 1030, a cost entry box 1035, a bookable impression field 1040, an order budget and available budget field 1045, and a CPM slider control 1005.

The order budget and available budget field 1045 may correspond to the total available budget specified in an advertiser order and the amount of the order that has not yet been committed. For example, an order budget of $1,000,000 may be specified in an advertiser order and $500,000 may have been previously utilized for purchasing placements on publisher web sites within a network leaving $500,000 available for booking impressions. Displaying the available budget in the price placement box enables the ad broker to quickly ascertain the amount of budget he may have to work with.

The impression goal entry box 1020, proposed CPM entry box 1030, and cost entry box 1035 may be utilized by the ad broker to specify the number of impressions desired, a proposed CPM for each impression, and a total cost associated with purchasing the desired impressions at the proposed CPM.

The bookable impression field 1040 may display the total number of impressions available for booking within a network. Displaying the total number of bookable impressions available may enable the ad broker to ascertain the maximum number of impressions he may have to work with.

The impression slider control 1005 may include a chart 1010, a slider control 1025, and a proposed CPM value entry box 1050. The vertical axis of the chart 1010 may correspond to the number of available impressions and the horizontal axis may correspond to a CPM price. As shown, the number of bookable impressions available within a network may increase with the CPM price. This may occur because the number of publishers willing to sell advertisement space may increase with the CPM price. The volume of bookable impressions may therefore increase accordingly.

A desired number of impressions may be specified via the slider control 1025. A threshold line 1055 corresponding to the desired number of impressions may be shown on the chart and may be vertically aligned with the position of the slider control 1025. Raising and lowering the slider control 1025 may raise and lower the threshold line 1055 and therefore the number of impressions desired. The cost in terms of CPM for booking the impressions may be displayed in the proposed CPM value entry box 1050. The cost may vary accordingly as the slider control 1025 is raised and lowered. The values shown within the impression goal entry box 1020, proposed CPM entry box 1030, and cost entry box 1035 may vary as the slider control is adjusted. The impression goal entry box 1020 and proposed CPM value entry box 1030 may display the values specified via the impression slider control 1005. The value shown in the cost entry box 1035 may be computed via the following equation:

$$\text{NumOfImpressions} \times \text{proposed CPM} = \text{Cost}$$

Alternatively, the values shown within the impression goal entry box 1020, proposed CPM entry box 1030, and cost entry box 1035 may be specified. In this case, the impression goal slider control 1005 may be updated automatically to reflect the various values. As described above with reference to FIG. 7, the various values may be locked and unlocked so as to lock the value of a particular parameter. Providing a graphical control for displaying the number of impressions available at different proposed CPM prices may enable the ad broker to quickly determine the number of impressions available at different price points. This in turn may allow for more efficient use of an advertising budget.

Returning to FIG. 9, the ad broker may add the network to the ad group region 910. The name of the network may be displayed in the network column 995. The category within which publisher web site within the network may be categorized may be shown in the category column 950. The position and dimension column 955 and 960 may display the position and dimensions of an advertisement region within a web page for displaying advertisements. The flight dates columns 965 may correspond to a date range for displaying an advertisement within the network. The proposed CPM price, impression goal and cost associated with booking impressions within each network may be shown in the CPM column 970, impression column 975, and cost column 980 respectively. These values may correspond to the values specified via the network price placement box 1000 (FIG. 10) described above. The network information in the ad group region 910 may then be saved under an ad group name. Additional operations, such as those described with reference to FIG. 5 above, may be performed on the ad group. For example, the ad group may be renamed or cloned and advertisements may be associated with the ad group.

Figure 11:
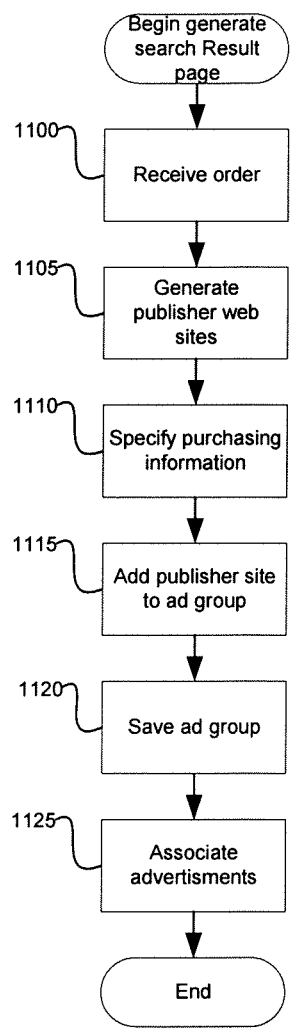
FIG. 11 is a flow diagram for matching advertiser advertisements to publisher web sites.

FIG. 11 is a flow diagram for matching advertiser advertisements to publisher web sites. At block 1100, an advertiser order may be communicated. The advertiser order may include an advertisement as well as audience targeting information. For example, the audience targeting information may correspond to advertising space region information, demographic information, behavioral information, geographic information, technology information, and web site content information as described above. At block 1105, a list of publisher web sites that target audiences that match the audience targeting information along with various attributes associated with the publisher web sites may be displayed. For example, as described above with reference to FIG. 5, the name, category, number of bookable impressions available, and rate card information for each publisher web site may be displayed.

At block 1110, publisher web sites may be selected and purchasing information specified. The purchasing information may correspond to a number of impressions purchased and a proposed CPM price corresponding to a cost per 1000 impressions. The total cost associated with purchasing the impressions may be calculated according to the following equation:

$$\text{NumOfImpressions} \times \text{proposed CPM} = \text{total cost}$$

At block 1115, the selected publisher web sites may be added to an ad group. Information in the ad group may be displayed. For example, as described above with reference to FIG. 5, the name, categories, advertisement location and dimensions, flight dates for the advertisements, proposed CPM, impression goal and cost associated with each publisher web site may be shown. At block 1120, the ad group may be saved. For example, the ad group may be saved to the ad group database 320 shown in FIG. 3.

At block 1125, advertisements may be associated with the ad group. For example, via a user interface, such as the ad group manager user interface 800 shown in FIG. 8, advertisements may be associated with the ad group.

Figure 12:
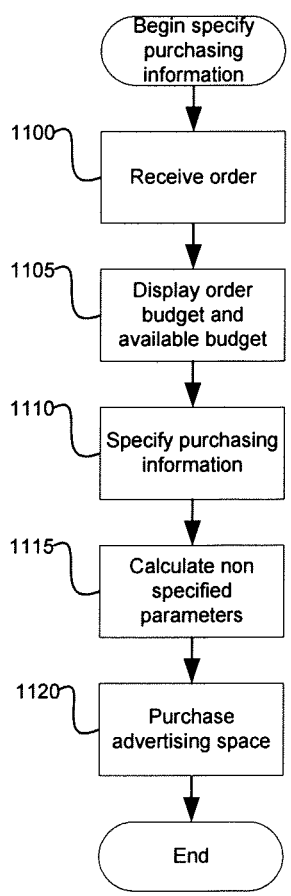
FIG. 12 is a flow diagram for specifying purchasing information.

FIG. 12 is a flow diagram for specifying purchasing information for purchasing advertisement placements from publishers. The actions shown in the flow diagram may occur at block 1110 of FIG. 11. Referring to FIG. 12, at block 1100, order information may be communicated from an advertiser. The order information may specify the advertiser's total budget. At block 1105, the order budget in the order and the available budget may be displayed via a user interface, such as the price placement user interface 700 shown in FIG. 7. The available budget may correspond to the amount of the order budget available for purchasing advertising space. The available budget may be lower than the order budget because advertisement placements may have been previously purchased. The number of bookable impressions and rate card information communicated from the publisher may also be displayed.

At block 1110, the ad broker may specify the desired number of impressions, the proposed cost per impression, and/or the total cost available for purchasing the impressions on a publisher web site. For example, the ad broker may utilize the price placement user interface 700 shown in FIG. 7 to specify the parameters. At block 1115, non-specified parameters may be calculated based on the specified parameters. The parameters may be related by the following equation:

$$\text{Desired number of impressions} \times \text{proposed cost per impression} = \text{total cost}$$

Parameters that the ad broker may wish to fix may be locked. For example, as shown FIG. 7, an impression goal lock 730, proposed CPM lock 735, and cost lock 740 may be utilized to lock parameters the ad broker wishes to fix and to unlock parameters so that they may be calculated.

At block 1120, advertisement placements may be purchased on the publisher web site and the available budget may be decreased by the total cost calculated above. The total number of available impressions on the publisher web site may also be decreased. Displaying the order budget and available budget along with the number of bookable impressions and the rate card information may enable the ad broker to quickly determine how many impressions to purchase and an optimal price for the impressions. Providing parameter locks may enable the ad broker to lock important parameters and automatically calculate less important parameters. This may further aid the ad broker in determining the number of impressions to purchase and the optimal price for the impressions.

Figure 13:
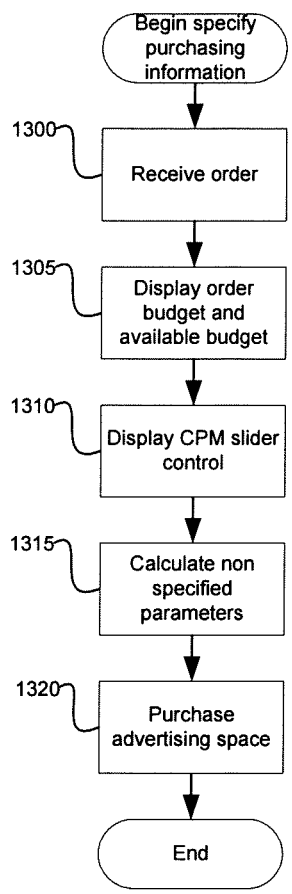
FIG. 13 is a flow diagram for specifying purchasing information in a second embodiment.

FIG. 13 is a flow diagram for specifying purchasing information in a second embodiment. The actions shown in the flow diagram may be utilized when purchasing placements across a network as described above with reference to FIGS. 9 and 10 above. At block 1300, order information may be communicated from an advertiser. The order information may specify the advertiser's total budget. At block 1305, the order budget in the order and the available budget may be displayed via a user interface, such as the network price placement user interface 1000 shown in FIG. 10. The available budget may correspond to the amount of the order budget available for purchasing advertising space. The available budget may be lower than the order budget because advertisement placements may have been previously purchased. The number of bookable impressions may also be displayed.

At block 1310, a control that provides a visual representation of the number of impressions available versus the proposed cost per impression may be displayed. The control may correspond to the CPM slider control 1005 in the network price placement user interface 1000 shown in FIG. 10. The control may include a chart. The upper value of the vertical access of the chart may correspond to the number of bookable impressions available within the network and the horizontal access may correspond to the proposed cost per impression. The upper and lower bounds of the horizontal access may correspond to rate card information provided by the network operator.

The control may also include a slider control that may be utilized to specify the number of impressions desired. A proposed CPM value entry box may also be shown and may display the cost associated with the number of impressions desired. An impression goal entry box, a proposed CPM entry box, and cost entry box may also be displayed.

At block 1315, the CPM slider control may be adjusted so as to obtain a desired number of impressions at a desired proposed cost per impression. The value shown in the proposed CPM value entry box may change when the slider control position is changed. The values shown in the impression goal entry box, the proposed CPM entry box, and the cost entry box may also change when the slider control position is changed. The cost may be calculated based on the number of impressions desired and the cost per impression.

At block 1320, advertisement placements may be purchased within the network and the available budget may be decreased by the total cost calculated above. Providing a graphical control for displaying the number of impression available at different proposed CPM prices may enable the ad broker to quickly determine the number of impressions available at different price points. This in turn may allow for more efficient use of an advertising budget.

Figure 14:
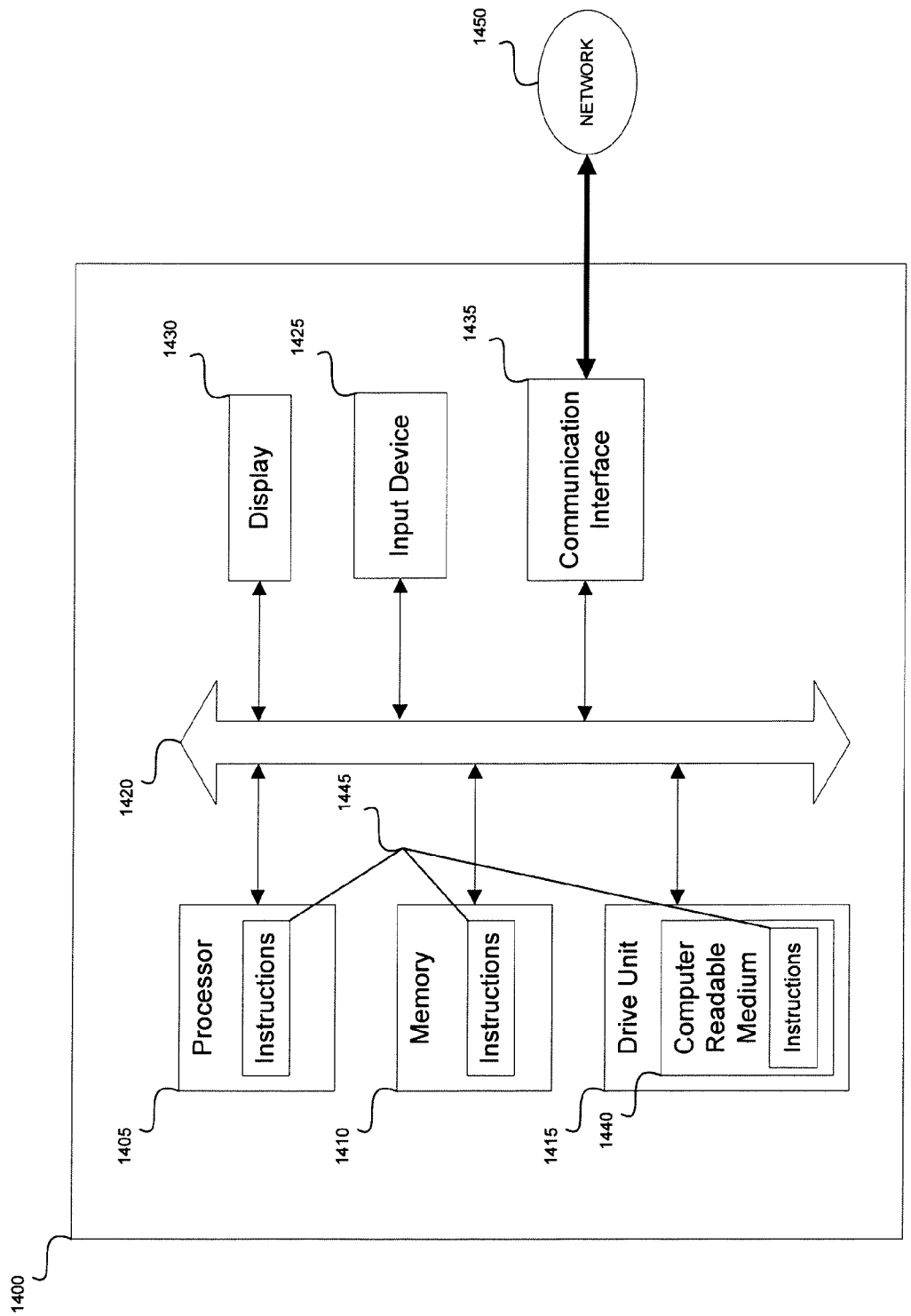
FIG. 14 illustrates a general computer system, which may represent any of the computing devices referenced herein.

FIG. 14 illustrates a general computer system, which may represent the computer 305 in FIG. 3, an ad server 410, a publisher web server 405, user terminal or any of the other computing devices referenced herein. The computer system 1400 may include a set of instructions 1445 that may be executed to cause the computer system 1400 to perform any one or more of the methods or computer based functions disclosed herein. The computer system 1400 may operate as a standalone device or may be connected, e.g., using a network, to other computer systems or peripheral devices.

In a networked deployment, the computer system may operate in the capacity of a server or as a client user computer in a server-client user network environment, or as a peer computer system in a peer-to-peer (or distributed) network environment. The computer system 1400 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions 1445 (sequential or otherwise) that specify actions to be taken by that machine. In one embodiment, the computer system 1400 may be implemented using electronic devices that provide voice, video or data communication. Further, while a single computer system 1400 may be illustrated, the term "system" shall also be taken to include any collection of systems or sub-systems that individually or jointly execute a set, or multiple sets, of instructions to perform one or more computer functions.

As illustrated in FIG. 14, the computer system 1400 may include a processor 1405, such as, a central processing unit (CPU), a graphics processing unit (GPU), or both. The processor 1405 may be a component in a variety of systems. For example, the processor 1405 may be part of a standard personal computer or a workstation. The processor 1405 may be one or more general processors, digital signal processors, application specific integrated circuits, field programmable gate arrays, servers, networks, digital circuits, analog circuits, combinations thereof, or other now known or later developed devices for analyzing and processing data. The processor 1405 may implement a software program, such as code generated manually (i.e., programmed).

The computer system 1400 may include a memory 1410 that can communicate via a bus 1420. For example, the advertisement listing database 110, database with website links 140, and multimedia advertisement database may be stored in the memory. The memory 1410 may be a main memory, a static memory, or a dynamic memory. The memory 1410 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, the memory 1410 may include a cache or random access memory for the processor 1405. Alternatively or in addition, the memory 1410 may be separate from the processor 1405, such as a cache memory of a processor, the system memory, or other memory. The memory 1410 may be an external storage device or database for storing data. Examples may include a hard drive, compact disc ("CD"), digital video disc ("DVD"), memory card, memory stick, floppy disc, universal serial bus ("USB") memory device, or any other device operative to store data. The memory 1410 may be operable to store instructions 1445 executable by the processor 1405. The functions, acts or tasks illustrated in the figures or described herein may be performed by the programmed processor 1405 executing the instructions 1445 stored in the memory 1410. The functions, acts or tasks may be independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

The computer system 1400 may further include a display 1430, such as a liquid crystal display (LCD), an organic light emitting diode (OLED), a flat panel display, a solid state display, a cathode ray tube (CRT), a projector, a printer or other now known or later developed display device for outputting determined information. The display 1430 may act as an interface for the user to see the functioning of the processor 1405, or specifically as an interface with the software stored in the memory 1410 or in the drive unit 1415.

Additionally, the computer system 1400 may include an input device 1430 configured to allow a user to interact with any of the components of system 1400. The input device 1425 may be a number pad, a keyboard, or a cursor control device, such as a mouse, or a joystick, touch screen display, remote control or any other device operative to interact with the system 1400.

The computer system 1400 may also include a disk or optical drive unit 1415. The disk drive unit 1415 may include a computer-readable medium 1440 in which one or more sets of instructions 1445, e.g. software, can be embedded. Further, the instructions 1445 may perform one or more of the methods or logic as described herein. The instructions 1445 may reside completely, or at least partially, within the memory 1410 and/or within the processor 1405 during execution by the computer system 1400. The memory 1410 and the processor 1405 also may include computer-readable media as discussed above.

The present disclosure contemplates a computer-readable medium 1440 that includes instructions 1445 or receives and executes instructions 1445 responsive to a propagated signal; so that a device connected to a network 1450 may communicate voice, video, audio, images or any other data over the network 1450. The instructions 1445 may be implemented with hardware, software and/or firmware, or any combination thereof. Further, the instructions 1445 may be transmitted or received over the network 1450 via a communication interface 1435. The communication interface 1435 may be a part of the processor 1405 or may be a separate component. The communication interface 1435 may be created in software or may be a physical connection in hardware. The communication interface 1435 may be configured to connect with a network 1450, external media, the display 1430, or any other components in system 1400, or combinations thereof. The connection with the network 1450 may be a physical connection, such as a wired Ethernet connection or may be established wirelessly as discussed below. Likewise, the additional connections with other components of the system 1400 may be physical connections or may be established wirelessly.

The network 1450 may include wired networks, wireless networks, or combinations thereof. Information related to business organizations may be provided via the network 1450. The wireless network may be a cellular telephone network, an 802.11, 802.16, 802.20, or WiMax network. Further, the network 1450 may be a public network, such as the Internet, a private network, such as an intranet, or combinations thereof, and may utilize a variety of networking protocols now available or later developed including, but not limited to TCP/IP based networking protocols.

The computer-readable medium 1440 may be a single medium, or the computer-readable medium 1440 may be a single medium or multiple media, such as a centralized or distributed database, and/or associated caches and servers that store one or more sets of instructions. The term "computer-readable medium" may also include any medium that may be capable of storing, encoding or carrying a set of instructions for execution by a processor or that may cause a computer system to perform any one or more of the methods or operations disclosed herein.

The computer-readable medium 1440 may include a solid-state memory such as a memory card or other package that houses one or more non-volatile read-only memories. The computer-readable medium 1440 also may be a random access memory or other volatile re-writable memory. Additionally, the computer-readable medium 1440 may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that may be a tangible storage medium. Accordingly, the disclosure may be considered to include any one or more of a computer-readable medium or a distribution medium and other equivalents and successor media, in which data or instructions may be stored.

Alternatively or in addition, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system may encompass software, firmware, and hardware implementations.

Accordingly, the method and system may be realized in hardware, software, or a combination of hardware and software. The method and system may be realized in a centralized fashion in at least one computer system or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The method and system may also be embedded in a computer program product, which included all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

From the foregoing, it may be seen that the embodiments disclosed herein provide an approach for organizing an advertising campaign and booking advertisement placements on publisher web sites and networks of publisher web sites. For example, publisher web sites and networks of publisher web sites may be grouped into various ad groups. The publisher web sites and/or publisher web sites within a network may share attributes that may enable targeting a particular audience. Further, providing a graphical user interface that enables determining the number of impressions available at a given price per impression may enable an ad broker to quickly book advertisement across various publisher web sites and/or various networks of publisher web sites. This may enable the ad broker to maximize an advertiser's return on investment.

While the method and system has been described with reference to certain embodiments, it will be understood by those skilled in the art that various changes may be made and equivalents may be substituted without departing from the scope. In addition, many modifications may be made to adapt a particular situation or material to the teachings without departing from its scope. Therefore, it is intended that the present method and system not be limited to the particular embodiment disclosed, but that the method and system include all embodiments falling within the scope of the appended claims.

We claim:

1. A method for organizing an advertising campaign in an Internet environment, the method comprising:
displaying, on a display device, a list of website names and purchasing information, wherein the website names represent websites configured to display advertisements and the purchasing information defines terms for placing advertisements on the websites, and wherein the websites have attributes that match received selection criteria;
receiving, by a computer, data that defines a selection of at least one website in the list and purchasing information for purchasing advertising space on the at least one website;
adding the at least one website and the purchasing information to an ad group that defines a group of websites that have attributes that match the received selection criteria;
displaying, on the display device, a website name and purchasing information associated with the at least one website; and
storing, by the computer, the ad group to a memory device.

2. The method according to claim 1, wherein the received selection criteria includes at least one of: advertising space position information, demographic information, behavioral information, geographic information, technology information, and website content information.

3. The method according to claim 1, wherein the purchasing information includes a number of impressions purchased and a price amount corresponding to a cost per impression.

4. The method according to claim 3, further comprising calculating a total number of impressions purchased and total price of the ad group.

5. The method according to claim 1, further comprising displaying, on the display device, websites in the ad group arranged so that at least some of the attributes of the websites are displayed simultaneously with the website names.

6. The method according to claim 1, further comprising copying the websites in the ad group to another ad group.

7. The method according to claim 1, further comprising deleting websites in the ad group.

8. A method for communicating advertisements in an Internet environment, the method comprising:
adding, by a processor, a publisher website name of a publisher website from a displayed list of website names to a group of publisher website names so as to create an ad group, where publisher websites in the ad group share attributes and are configured to display advertisements;
receiving, at the processor, from a user, data that defines a selection of the ad group and data that defines one or more advertisements to be communicated to the publisher websites;
receiving, at the processor, a request to display an advertisement from a browser displaying a web page generated by the publisher website;
communicating, by the processor, at least one of the one or more advertisements to the browser.

9. The method according to claim 8, wherein the shared attributes correspond to at least one of: advertising space position attributes, demographic attributes, behavioral attributes, geographic attributes, technology attributes, and website content attributes.

10. A method for organizing an advertising campaign in an Internet environment, the method comprising:
- receiving, at a processor, data that defines an indication from a user to add a publisher website from a displayed list of websites to a group of publisher websites so as to create a first ad group, where publisher websites in the first ad group share attributes and are configured to display advertisements;
- saving, by the processor, the first ad group to a memory;
- specifying, by the processor, one or more advertisements to be communicated to publisher web sites of the first ad group.

11. The method according to claim 10, further comprising:
- retrieving, by the processor, the first ad group;
- adding, by the processor, additional publisher websites to the first ad group; and
- saving, by the processor, the ad group.

12. The method according to claim 10, further comprising:
- retrieving, by the processor, the first ad group;
- adding, by the processor, publisher websites to or deleting publisher websites from the first ad group;
- saving, by the processor, the first ad group under a different name so as to create a second ad group, where at least some of the publisher websites are different between the first and the second ad groups.

13. A non-transitory machine-readable storage medium having stored thereon, a computer program comprising at least one code section for organizing an advertising campaign in an Internet environment, the at least one code section being executable by a machine for causing the machine to perform acts of:
- displaying a list of website names and purchasing information, wherein the website names represent websites configured to display advertisements and the purchasing information defines terms for placing advertisements on the websites, and wherein the websites have attributes that match received selection criteria;
- receiving data that defines a selection of at least one website in the list and specifying purchasing information for purchasing advertising space on the at least one website;
- adding the at least one website and the purchasing information to an ad group that defines a group of websites that have attributes that match the received selection criteria;
- displaying a website name and purchasing information associated with the at least one website; and
- storing the ad group in a memory device.

14. The non-transitory machine-readable storage medium according to claim 13, wherein the received selection criteria includes at least one of: advertising space position information, demographic information, behavioral information, geographic information, technology information, and website content information.

15. The non-transitory machine-readable storage medium according to claim 13, wherein the purchasing information includes a number of impressions purchased and a price amount corresponding to a cost per impression.

16. The non-transitory machine-readable storage medium according to claim 15, wherein the at least one code section comprises code that enables calculating a total number of impressions purchased and total price of the ad group.

17. The non-transitory machine-readable storage medium according to claim 13, wherein the at least one code section comprises code that enables displaying, on a computer screen, websites in the ad group arranged so that at least some of the attributes of the websites are displayed simultaneously with the website names.

18. The non-transitory machine-readable storage medium according to claim 13, wherein the at least one code section comprises code that enables copying the websites in the ad group to another ad group.

19. The non-transitory machine-readable storage medium according to claim 13, wherein the at least one code section comprises code that enables deleting websites in the ad group.

20. A system for organizing an advertising campaign in an Internet environment, the system comprising:
- a processor configured to communicate to a computer screen a list of website names and purchasing information, wherein the website names represent websites configured to display advertisements and the purchasing information defines terms for placing advertisements on the websites, and wherein the websites have attributes that match received selection criteria;
- network circuitry configured to receive data that defines a selection of at least one website in the list and purchasing information for purchasing advertising space on the at least one website, wherein the processors is further configured to add the at least one website and the purchasing information to an ad group that defines a group of websites that have attributes that match the received selection criteria;
- the processor is further configured to display, on the computer screen, a website name and purchasing information associated with the at least one website; and
- a memory device in communication with the processor, wherein the processor is further configured to store the ad group to the memory device.

21. The system according to claim 20, wherein the received selection criteria includes at least one of: advertising space position information, demographic information, behavioral information, geographic information, technology information, and website content information.

22. The system according to claim 20, wherein the purchasing information includes a number of impressions purchased and a price amount corresponding to a cost per impression.

23. The system according to claim 22, wherein the processor is further configured to calculate a total number of impressions purchased and total price of the ad group.

24. The system according to claim 20, wherein the websites in the ad group communicated to the computer screen are arranged so that at least some of the attributes of the websites are displayed on the computer screen simultaneously with the website names.

25. The system according to claim 20, wherein the processor is further configured to copy the websites in the ad group to another ad group.

* * * * *